United States Patent
Simso

(10) Patent No.: US 6,939,368 B2
(45) Date of Patent: Sep. 6, 2005

(54) DELIVERY SYSTEM FOR SELF EXPANDING STENTS FOR USE IN BIFURCATED VESSELS

(75) Inventor: Eric J. Simso, Excelsior, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 374 days.

(21) Appl. No.: 10/053,298

(22) Filed: Jan. 17, 2002

(65) Prior Publication Data

US 2003/0135259 A1 Jul. 17, 2003

(51) Int. Cl.[7] .................................................. A61F 2/06
(52) U.S. Cl. ............................................................ 623/1.11
(58) Field of Search ............................... 623/1.11, 1.35; 606/108, 194, 200, 1.36

(56) References Cited

U.S. PATENT DOCUMENTS

| | | | |
|---|---|---|---|
| 4,655,771 A | 4/1987 | Wallsten | |
| 5,026,377 A | 6/1991 | Burton et al. | |
| 5,290,295 A | * 3/1994 | Querals et al. ............ | 623/1.23 |
| 5,662,675 A | 9/1997 | Polanskyj Stockert et al. | |
| 5,720,735 A | 2/1998 | Dorros | |
| 6,017,363 A | 1/2000 | Hojeibane | |
| 6,129,756 A | 10/2000 | Kugler et al. | |
| 6,142,973 A | 11/2000 | Carleton et al. | |
| 6,143,002 A | 11/2000 | Vietmeier | |
| 6,156,063 A | 12/2000 | Douglas | |
| 6,168,617 B1 | 1/2001 | Blaeser et al. ............. | 623/1.11 |
| 6,183,481 B1 | 2/2001 | Lee et al. | |
| 6,197,049 B1 | 3/2001 | Shaoilian et al. | |

FOREIGN PATENT DOCUMENTS

| | | |
|---|---|---|
| WO | WO 98/27894 | 7/1998 |
| WO | WO 99/34749 | 7/1999 |
| WO | WO 00/13613 | 3/2000 |
| WO | WO 00/71059 | 11/2000 |

* cited by examiner

*Primary Examiner*—(Jackie) Tan-Uyen T. Ho
(74) *Attorney, Agent, or Firm*—Vidas, Arrett & Steinkraus, P.A.

(57) ABSTRACT

A stent delivery catheter that comprises a central shaft having a distal tip extending therefrom, at least one guide wire, and a retractable sheath. The distal tip includes a proximal ridge which has a diameter larger than the central shaft. The guide wire includes at least one stent disposed about a portion thereof. The at least one guide wire being movable relative to the central shaft. The retractable sheath being disposed about the central shaft and the at least one guide wire. The retractable sheath having a distal edge removably engaged to the distal tip. The proximal ridge of the distal tip overlapping the distal edge of the retractable sheath. The retractable sheath being proximally retractable from the distal tip.

11 Claims, 6 Drawing Sheets

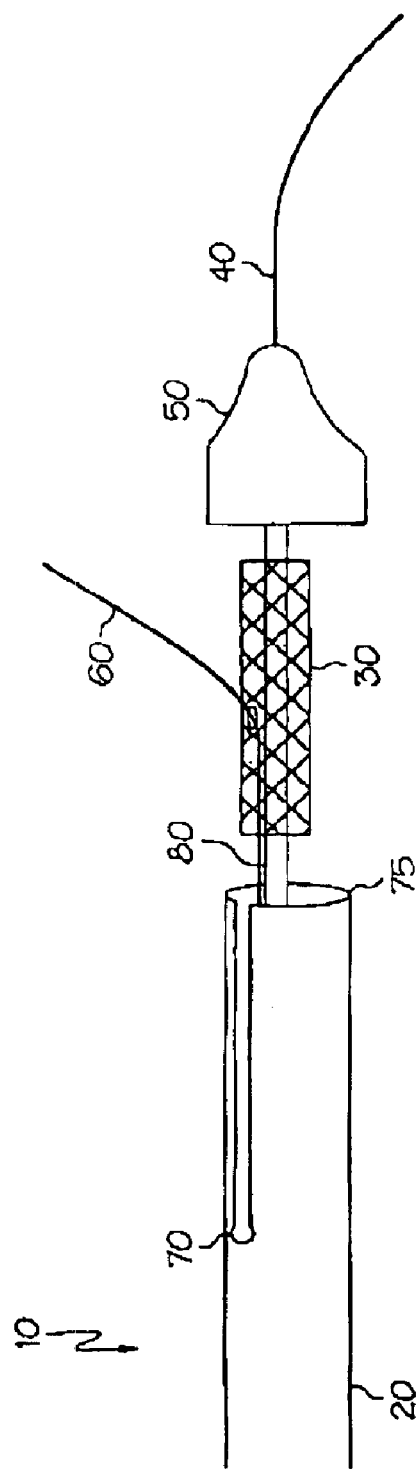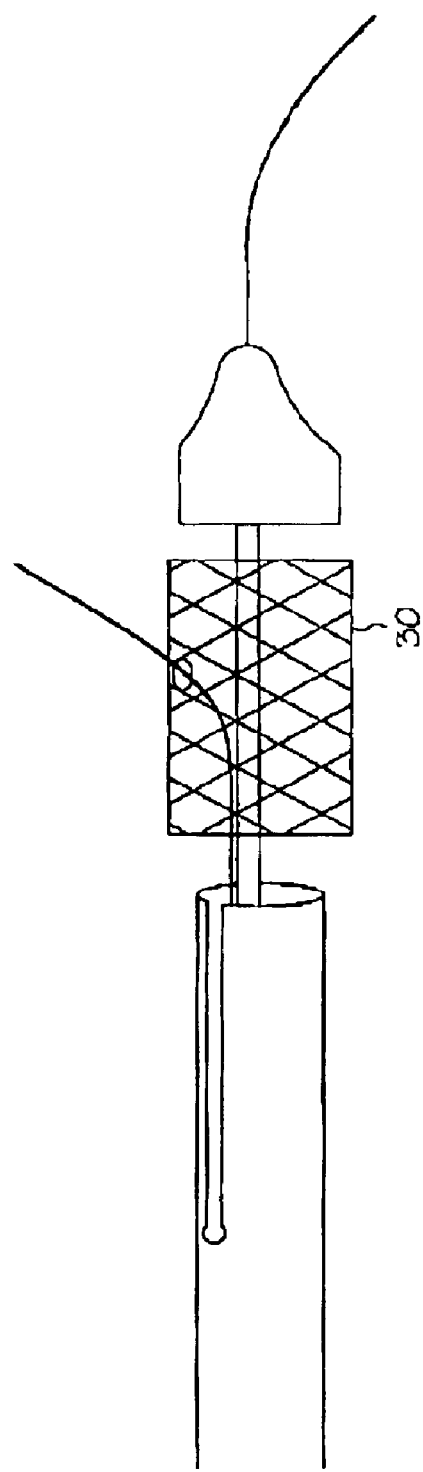

DELIVERY SYSTEM FOR SELF EXPANDING STENTS FOR USE IN BIFURCATED VESSELS

FIELD OF THE INVENTION

The present invention may be directed to many different embodiments. Some embodiments of the present invention relate to catheters and medical device delivery systems. At least one embodiment of the invention is directed to a delivery system and sheath for deploying self expanding stents and stent grafts used in treating stenotic lesions at bifurcations in body vessels without requiring multiple catheterizations.

BACKGROUND OF THE INVENTION

Stents or stent grafts are a form of transluminal prosthesis devices which are used to maintain, open or dilate stenotic lesions in body lumens which have been affected by disease. These prosthetic devices are typically either of two types including the balloon expandable and "self-expanding" varieties. Self expanding stents are inserted into the vascular system in a compressed or contracted state, are permitted to expand upon removal of a restraint typically referred to as a retractable sheath or sleeve. These stents are particularly advantageous for use because they may be formed of a shape memory alloy which is both resistant to compression and also has the ability to return to its previous shape. NITINOL is a shape memory alloy that is commonly used in stents and stent grafts. Alternative forms of self-expanding stents also exist which are not made of NITINOL such as the Wallstent® Endoprosthesis. In addition to metals, stents may also be formed of biodegradable materials.

It is often the case that a stenotic lesion occurs at a branch or bifurcation in a vessel. Placement and deployment of these prosthetic devices at bifurcations can be much more problematic. One current technique is to deploy a tubular stent having an opening across the bifurcation for placing a second stent through. Once the first stent is deployed, then the physician must then advance the second stent through the first stent.

It is advantageous in the case of bifurcations to utilize two separate guide wires to access the lesion and for positioning of each of the prosthetic devices used in the procedure including the second stent which is placed in the side branch.

This approach is advantageously used for positioning and deployment of balloon expandable stents. In the case of balloon expandable stents, the first stent, mounted on its delivery balloon is advanced over both the first guide wire and the second guide wire which exits from a hole in the mid-side portion of the stent and its balloon. This stent is then advanced to the first branch in the vessel at the region of the bifurcation and deployed. A second stent may then be advanced along the second guide wire through the hole in the first stent and positioned in the second branch at the region of the bifurcation. In this fashion, both stents may be accurately positioned and fixed in place by expansion of the balloon without the need to move either guide wire.

This approach is more problematic in the case of self-expandable stents because these stents are constrained in their form by a sheath, also referred to in the art as a sleeve or housing, which must be retracted in order to deploy the stent. Traditional sheaths are not formed with a hole to allow for exit of the side branch guide wire. Furthermore, even if such a hole was present, retraction of the sheath would be impossible in a two wire delivery system for self expanding stents.

One solution to this problem has been to add a slot from the wire exit port to the distal end of the sheath which allows the sheath to be retracted without moving the wire. Alternatively, a preferential tear line could be formed to make the slot. WO 99/34749 describes a self-expanding bifurcation stent and a delivery sleeve and method of delivery of such stents. The system includes a self-expanding stent and a corresponding delivery sleeve adapted to house two guide wires, one of which exits from the distal end and a second of which exits from a side hole in the stent. The preferred embodiments replace the hole with a longitudinal or oval slot. See WO 99/34749, pages 8–9. However, while the slot is advantageous for housing the second guide wire, keeping the sheath together is problematic. WO 99/34749 describes reinforcing the rim of the slot to adequately constrain the stent prior to deployment.

The entire content of all patents, patent applications and publications listed herein are incorporated herein by reference.

SUMMARY OF THE INVENTION

As indicated above, the present invention is directed to many embodiments. In at least one embodiment, the invention is directed to a catheter delivery device comprising a sheath which is specially adapted for delivery and deployment of a stent, wherein the stent is specially adapted for use into a bifurcated vessel which has a first branch and a second branch. The catheter employs a novel distal tip for securing a sheath thereto prior to stent delivery. The sheath is an elongate tubular member for housing a first and second guide wire lumen and a first and second guide wire. The sheath is adapted for use with a stent specially adapted for use in a bifurcated vessel by providing an outlet hole and or slit at the distal end of the sheath for exit of one or more guide wires into the first branch of the bifurcated vessel. The outlet may be further characterized as, weakened groove, perforation or the like. A weakened groove may be cut by the guide wire upon retraction of the sheath. In either instance, the guide wire does not hinder retraction of the sheath nor does the guide wire become trapped under the sheath upon retraction.

The distal tip overlaps the distal end of the slitted, grooved or perforated sheath holding the sheath together and consequently maintaining the stent properly in its unexpanded state. This configuration allows the wire to remain in place as the sheath is retracted and the stent is deployed decreasing the likelihood that the stent will move out of position upon retraction.

The device of the present invention maintains the flexibility of a sheath which does not require reinforcement and allows for excellent trackability and maneuverability of the device through body lumen.

BRIEF DESCRIPTION OF THE DRAWINGS

FIG. 2 is a side view of the embodiment of the invention depicted in FIG. 1 prior to stent deployment.

FIG. 3 is a side view of the embodiment of the invention depicted in FIG. 1 after stent deployment.

DETAILED DESCRIPTION OF THE PREFERRED EMBODIMENTS

Figure 1:
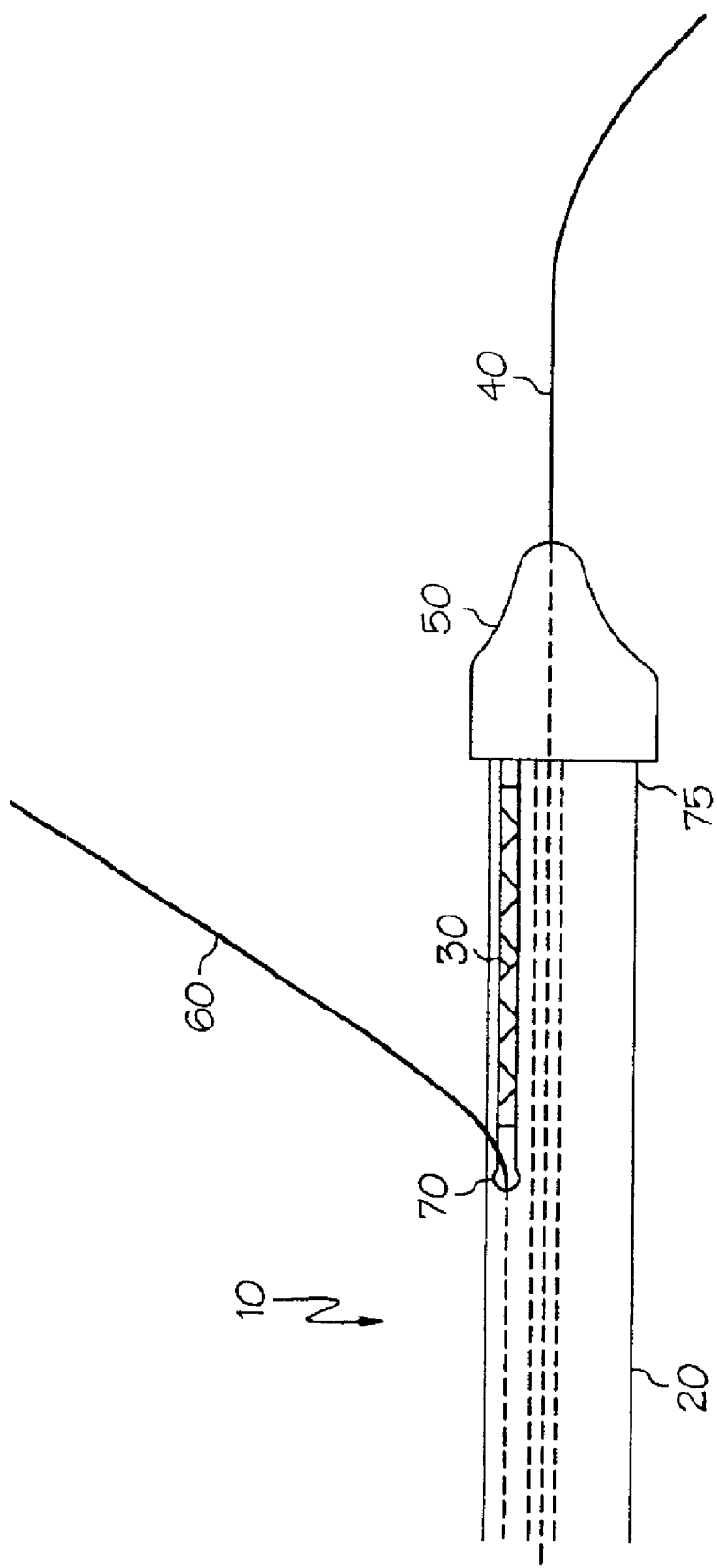
FIG. 1 is a side view of the self expanding stent delivery device of the present invention.

The stent delivery system of the present invention is designed for delivery and deployment of a bifurcated stent or multiple stents at a bifurcation in a body lumen. Represented in FIG. 1, the self expanding stent delivery system of the present invention is generally depicted by stent delivery system 10 where sheath 20 covers and holds first stent 30 in its unexpanded form. Stent 30 may be formed of any suitable medical grade material including stainless steel, shape memory alloys such as those of nickel titanium, polymers or biodegradable materials as are known in the art. Further stent 20 may be coated with drugs, genes or other materials known in the art which are intended to enhance efficacy. Sheath 20 may be formed of suitable medical polymers and may further include wire reinforcement (not shown).

First guide wire 40 exits the distal end of sheath 20 through tip 50. Guide wires 40 may be formed of any suitable medical grade alloy and may range in diameter from about 0.038–008" as is known in the art. Tip 50 may be formed of a suitable medical grade polymer. Tip 50 may further be formed of a polymer which is suitably soft to provide an atraumatic leading edge to stent delivery system 10. Alternatively, tip 50 may be formed of a hard plastic such as polycarbonate or metal where a strong or tuff tip is desired.

Second guide wire 60 is depicted exiting slit 70 in sheath 20. Slit 70 extends to distal end 75 of sheath 20. Slit 70 may also be formed by a perforation or weakened longitudinal portion of sheath 20. Distal end 75 may be covered by tip 50 such that tip 50 protects distal end 75 from snagging on any portion of the delivery system or the patient's vasculature. Tip 50 further holds slit 70 closed and thereby maintains stent 30 in its unexpanded state.

FIG. 2 depicts delivery system 10 where sheath 20 has been retracted relative to tip 50. Distal end 75 of sheath 20 is freely exposed and the second guide wire 60 has not been displaced from its location in the vasculature because of slit 70. As can be seen in FIG. 2, tip 50 is fixed to inner tube 80. Tube 80 may be formed of suitable medical polymers and may further include wire reinforcement (not shown). Tube 80 may further have a single lumen or multiple lumens configured to individually constrain wires 40 and 60 respectively. Tube 80 may have a side hole exit port for second guide wire 60. Second guide wire 60 may also exit a side hole provided in stent 30. However, wire 60 may also be threaded through any convenient opening in stent 30 according to the design configuration of stent 30. Tip 50 may be attached to tube 80 by adhesive, melt bonding or any other suitable technique. Alternatively, tip 50 may be molded to tube 80.

Figure 4:
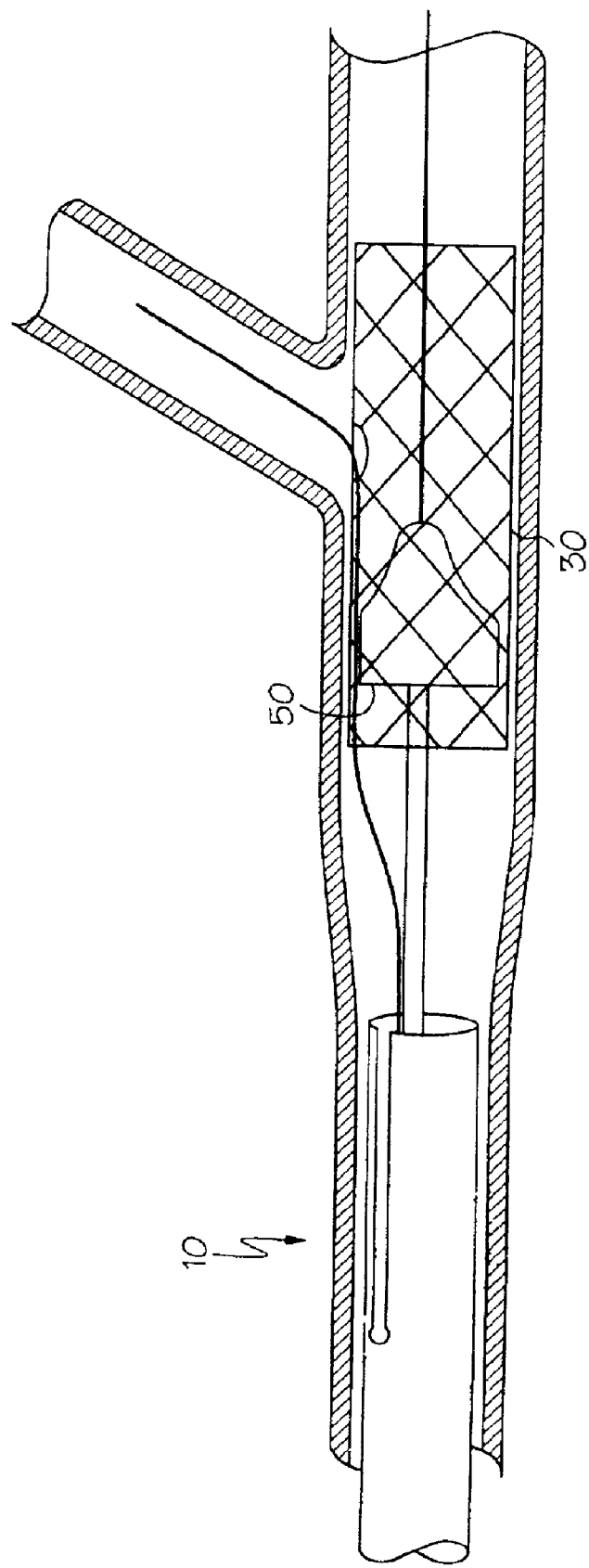
FIG. 4 is a side view of the embodiment of the invention depicted in FIG. 1 after stent deployment and withdrawal of the stent delivery system.

For illustrative purposes only, stent 30 is shown in its unexpanded form. However, in use stent 30 may expand immediately upon release of the constraining force of sheath 20. FIG. 3 depicts stent 30 where stent 30 has expanded from its unexpanded form. FIG. 4 depicts stent delivery system 10 after stent 30 has been fully deployed. Deployed stent 30 may have an expanded inside diameter larger then the outside diameter of tip 50 thereby allowing tip 50 to be withdrawn proximally through stent 30. Stent 30 may be further dilated using a balloon catheter (not shown) subsequent to the removal of delivery system 10 from the vasculature.

Figure 5:
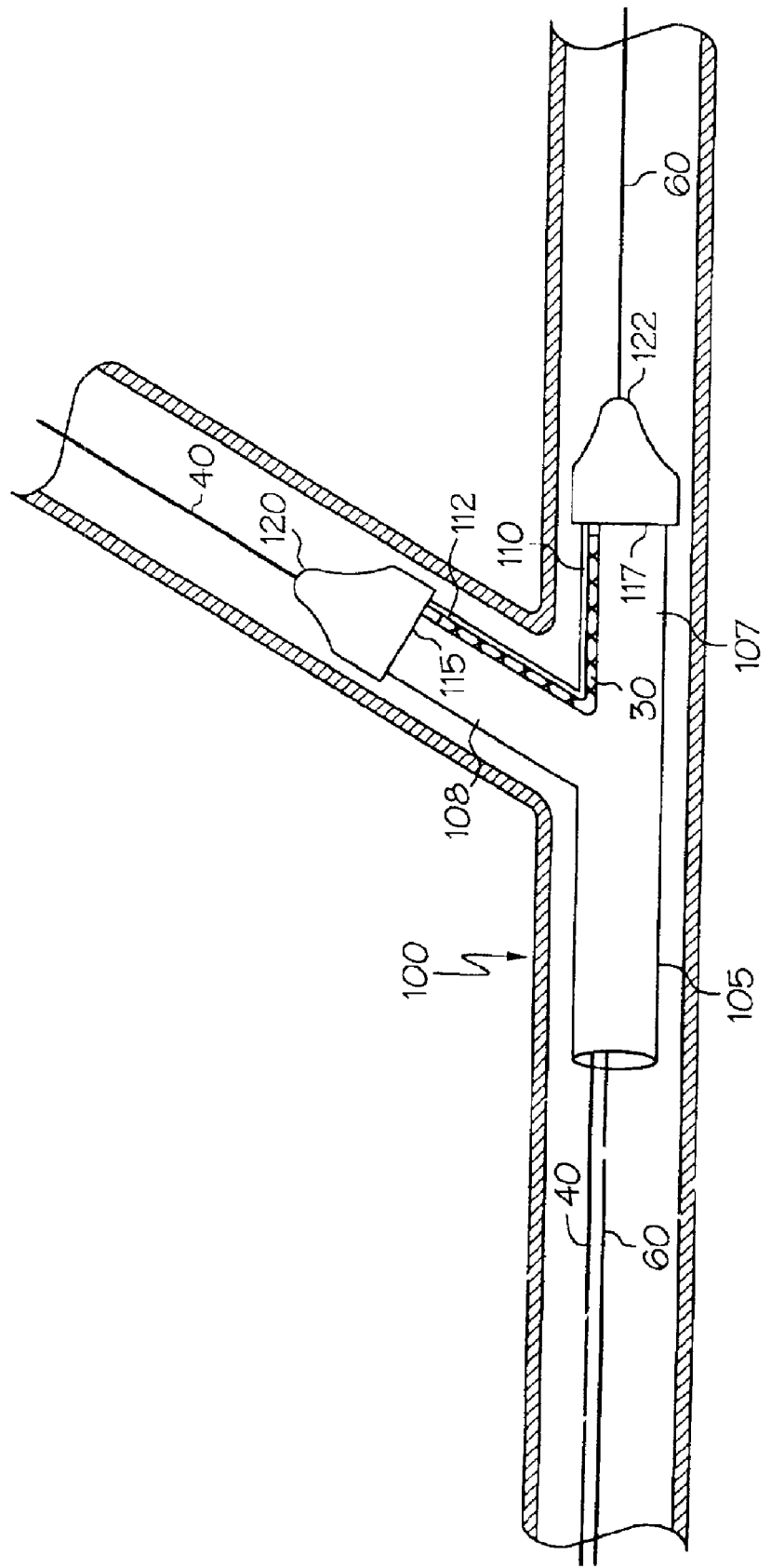
FIG. 5 is a side view of an alternative embodiment of the self expanding stent delivery device of the present invention.

In another embodiment of the invention, FIG. 5 depicts stent delivery system 100. Delivery system 100 has a proximal portion 105 which may bifurcate distally into a trunk portion 107 and a branch portion 108. The trunk portion 107 and branch portion 108 of delivery system 100 may each have slit depicted at 110 and 112 respectively. Slits 110 and 112 extend to the respective distal ends of trunk portion 107 and a branch portion 108. Slits 110 and 112 may also be formed by a perforation or weakened longitudinal portion of delivery system 100. Trunk portion 107 may have a distal end 117 and branch portion 108 may have a distal end 115. Distal ends 115 and 117 may be covered by tips 120 and 122 such that tips 120 and 122 protect distal ends 115 and 117 respectively from snagging on any portion of the delivery system or the patient's vasculature. Tips 120 and 122 further hold slits 110 and 112 closed and thereby maintains stent 30 in its unexpanded state.

Stent delivery system 100 may be formed of suitable medical polymers and may further include wire reinforcement (not shown). System 100 may further have a single lumen or multiple lumens configured to individually constrain wires 40 and 60 respectively. Tips 120 and 122 may be attached to system 100 by adhesive, melt bonding or any other suitable technique. Alternatively, tip 120 and 122 may be molded to system 100.

Figure 6:
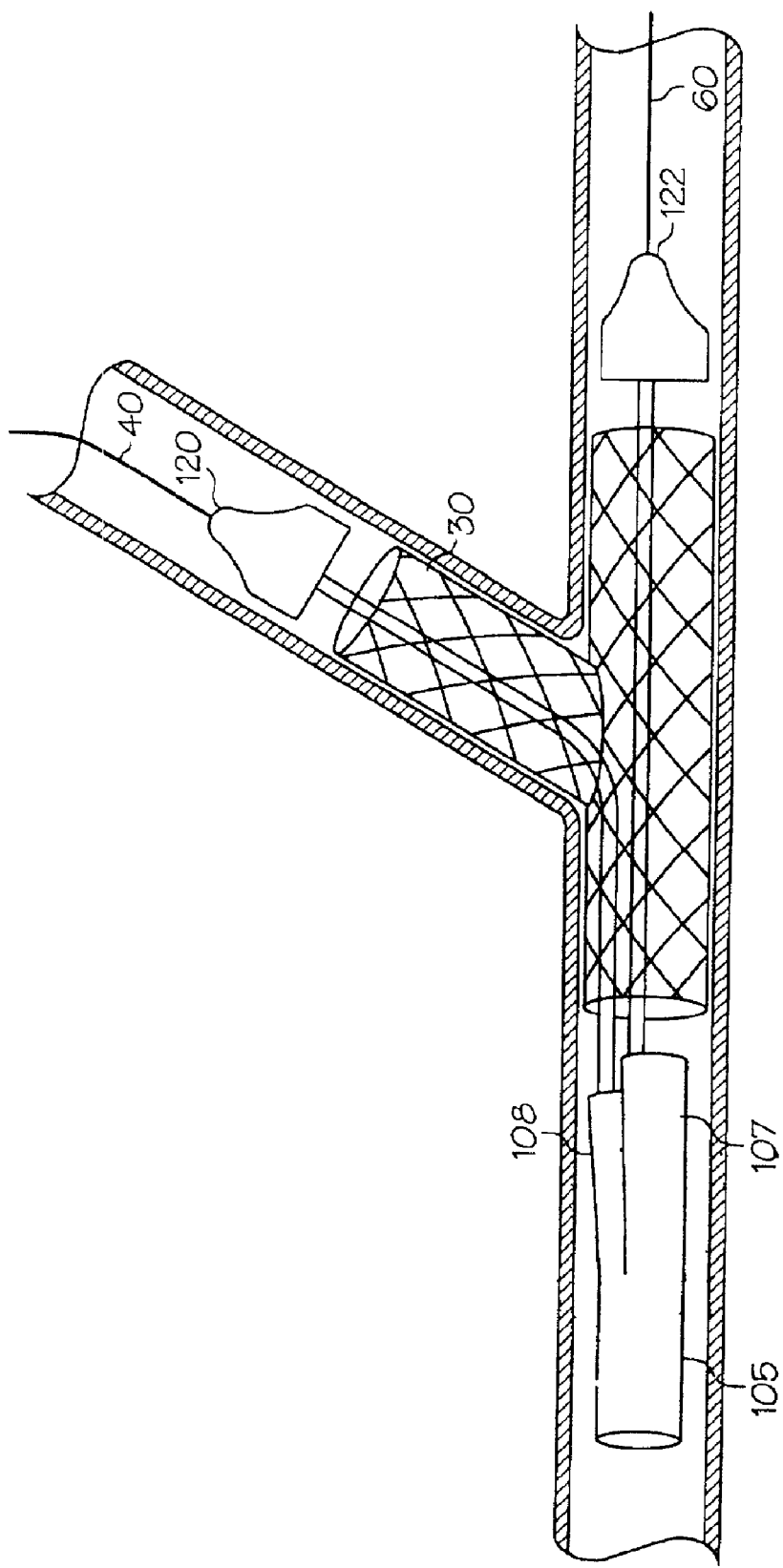
FIG. 6 is a side view of the embodiment of the invention depicted in FIG. 5 prior to stent deployment.
Figure 7:
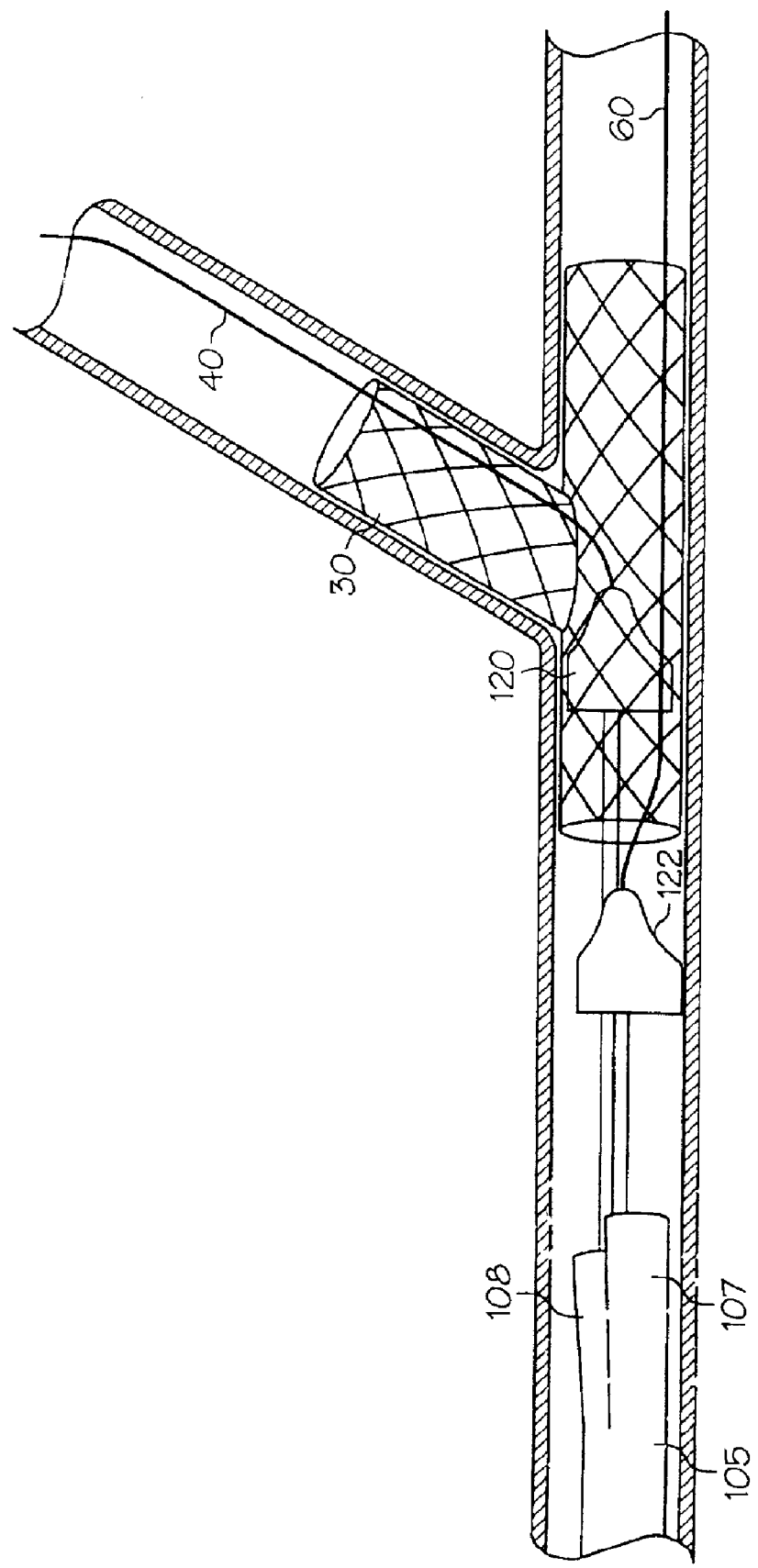
FIG. 7 is a side view of the embodiment of the invention depicted in FIG. 5 after deployment of the stent.

FIG. 6 depicts stent delivery system where trunk portion 107 and branch portion 108 have been retracted proximally relative to tips 120 and 122 and relative to stent 30. Similar to other embodiments herein, stent 30 may have a variety of configurations and be made of a variety of materials as described above. In use stent 30 may expand immediately upon release of the constraining force of branch portions 107 and 108. FIG. 6 depicts stent 30 where stent 30 has expanded from its unexpanded form. FIG. 7 depicts stent delivery system 100 after stent 30 has been fully deployed. Deployed stent 30 may have an expanded inside diameter larger then the outside diameter of tips 120 and 122 thereby allowing tips 120 and 122 to be withdrawn proximally through stent 30. Stent 30 may be further dilated using a balloon catheter (not shown) subsequent to the removal of delivery system 100 from the vasculature.

This completes the description of the embodiments of the invention. Those skilled in the art may recognize other equivalents to the specific embodiment described herein where such equivalents are intended to be encompassed by the claims attached hereto.

What is claimed is:

1. A catheter comprising:

a central shaft;

at least one guide wire movably positioned adjacent to the central shaft;

at least one stent disposed about a distal portion of the at least one guide wire, having an unexpanded state and an expanded state, the stent comprising a plurality of cells;

a removable sheath having a wall portion, the removable sheath being disposed about the at least one stent in the unexpanded state, the removable sheath constructed and arranged to retain the at least one stent in the unexpanded state, the removable sheath being retractable to allow the at least one stent to expand from the unexpanded state to the expanded state, the sheath having a distal end, the wall portion having at least one opening, the at lease one guide wire passing through the at least one opening;

and a distal tip overlapping the distal end of said sheath for holding said sheath together;

wherein the at least one guide wire passes through a cell of the stent.

2. The catheter of claim 1 wherein the at least one stent is bifurcated.

3. The catheter of claim 1 wherein the at least one opening extends from a predetermined position on the removable sheath to the distal end of the removable sheath.

4. The catheter of claim 1 wherein the at least one opening is selected from the group consisting of a slit, zipper, groove, hole and any combination thereof.

5. The catheter of claim 1 wherein the at least one opening extends to said distal end of said removable sheath by a groove that is formed by the at least one guide wire upon retraction of said removable sheath.

6. The catheter of claim 1 wherein said distal tip is connected to said central shaft, at least a portion of the distal tip overlapping the distal end of the removable sheath prior to retraction of the removable sheath.

7. A catheter comprising:

a central shaft;

a first guide wire, the first guide wire being movably positioned within the central shaft;

a stent disposed about a distal portion of the central shaft, the stent having an unexpanded state and an expanded state, the stent comprising a plurality of cells;

a removable sheath having a wall portion, the removable sheath being disposed about the stent in the unexpanded state, the removable sheath constructed and arranged to retain the stent in the unexpanded state, the removable sheath being retractable to allow the stent to expand from the unexpanded state to the expanded state, the wall portion having an opening therethrough;

a second guide wire, the second guide wire being movably positioned adjacent to the central shaft, the second guide wire passing through the opening of the wall portion of the sheath and through a cell of the stent;

and a tip overlapping a distal end of said sheath.

8. The catheter of claim 7, wherein the stent is bifurcated.

9. The catheter of claim 7, wherein the opening extends from a predetermined position on the removable sheath to the distal end of the said sheath.

10. The catheter of claim 7, wherein the opening is selected from a group consisting of a slit, zipper, groove, hole and any combination thereof.

11. The catheter of claim 7, wherein the opening extends to the distal end of said removable sheath by a groove that is formed by the second guide wire upon retraction of said removable sheath.

* * * * *